(12) United States Patent
Gallem

(10) Patent No.: US 6,513,519 B2
(45) Date of Patent: Feb. 4, 2003

(54) INHALATION ATOMIZER WITH A ONE-PIECE VALVE ELEMENT

(75) Inventor: Thomas Gallem, Munich (DE)

(73) Assignee: Pari GmbH Spezialsten fur effective Inhalation, Starnberg (DE)

( * ) Notice: Subject to any disclaimer, the term of this patent is extended or adjusted under 35 U.S.C. 154(b) by 0 days.

(21) Appl. No.: 09/745,295

(22) Filed: Dec. 20, 2000

(65) Prior Publication Data

US 2001/0013341 A1 Aug. 16, 2001

(30) Foreign Application Priority Data

Dec. 22, 1999 (DE) .......................... 199 62 110

(51) Int. Cl.⁷ ............................................ A61M 11/00
(52) U.S. Cl. .......................... 128/200.14; 128/200.21; 128/200.18; 128/207.12; 128/207.16
(58) Field of Search ................. 128/200.21, 200.14, 128/200.16, 200.18, 200.23, 207.12, 207.16, 201.28

(56) References Cited

U.S. PATENT DOCUMENTS

| | | |
|---|---|---|
| 2,470,297 A | 5/1949 | Fields |
| 3,848,583 A | 11/1974 | Parr |
| 3,870,046 A | 3/1975 | Elliott |
| 3,938,511 A | 2/1976 | Roberts |
| 4,441,494 A | 4/1984 | Montalbano |
| 4,456,016 A | 6/1984 | Nowacki et al. |
| 4,884,564 A | 12/1989 | Lamont |
| 5,349,947 A | 9/1994 | Newhouse et al. |
| 5,385,140 A | 1/1995 | Smith |
| 5,427,089 A | 6/1995 | Kraemer |
| 5,584,285 A | 12/1996 | Salter et al. |
| 5,586,551 A | 12/1996 | Hilliard |
| 5,645,049 A | 7/1997 | Foley et al. |
| 5,687,912 A | * 11/1997 | Denyer ...................... 239/343 |
| 5,813,401 A | 9/1998 | Radcliff et al. |
| 5,881,718 A | 3/1999 | Mortensen et al. |
| 6,129,080 A | * 10/2000 | Pitcher et al. ......... 128/200.21 |
| 6,131,568 A | * 10/2000 | Denyer et al. ......... 128/200.21 |

FOREIGN PATENT DOCUMENTS

| | | |
|---|---|---|
| DE | 24 02 192 | 1/1974 |
| EP | 0 626 180 | 11/1994 |

* cited by examiner

Primary Examiner—Glenn K. Dawson
Assistant Examiner—Darwin P. Erezo
(74) Attorney, Agent, or Firm—Merchant & Gould P.C.

(57) ABSTRACT

The inhalation atomizer of the invention has a valve box, which is divided into two sub-chambers by a partition wall. The valve box is closed by a valve box cover. A one-piece valve element projects into both sub-chambers and closes the openings provided in the sub-chambers and in the valve box cover in dependence on the breathing of the patient.

9 Claims, 5 Drawing Sheets

INHALATION ATOMIZER WITH A ONE-PIECE VALVE ELEMENT

The invention refers to inhalation atomizers for atomizing liquid and/or solid substances.

Inhalation atomizers of this kind have an inlet valve via which ambient air flows into the inhalation atomizer during the inspiration process, and an outlet valve out of which the air exhaled by the patient into the inhalation atomizer flows. Here care has to be taken that the air respired into the inhalation atomizer does not transport any aerosol outwards, as otherwise the desired accuracy of dosage is not achieved. An inhalation atomizer of said kind is known for instance from EP 0 626 180 A1.

While the fundamental functions of the inlet valve and the outlet valve are desired, the individual components required for the construction and the function of the valves often present difficulties regarding the use by the patient. The valve elements of the inlet valve and the outlet valve may be lost or confused so that there is the danger that the inhalation atomizer cannot be used anymore or is operated improperly. And also with a view to the assembly of the inhalation atomizer, as small a number of components as possible is desirable which, moreover, are also easy to handle.

On the basis of these facts, the technical problem underlying the invention is to improve an inhalation atomizer with an inlet valve and outlet valve such that an easier and safe handling by the patient as well as an easier and cheaper assembly in the production is obtained without impairing the functions of the inlet valve and the outlet valve.

By the one-piece valve element it is guaranteed that the patient only has to insert one single valve element, which leads not only to a simplification of the handling by the patient but also results in a simplification of the assembly during manufacturing. The one-piece design of the valve element requires a two-part valve box. For that purpose the valve box is divided up by a partition wall into two sub-chambers into each of which a section of the one-piece valve element projects. On the one hand, the valve element effects in the one sub-chamber that the inspiration takes place only through the flow channel intended therefor, namely through the inhalation atomizer housing. Thereby the aerosol generated in the inhalation atomizer is inhaled by the patient. On the other hand, the valve element effects in the other sub-chamber that during expiration into the atomizer no air flows through the inhalation atomizer and transports aerosol with it outwards.

The invention is described in more and non-limiting detail in the following by means of an embodiment with reference to the drawings, in which:

FIG. 1 is a first view of the inventive inhalation atomizer with a closed valve box.

FIG. 2 is a second view of the inventive inhalation atomizer with a removed valve box cover, but with an inserted valve element.

FIG. 3 is a third view of the inventive inhalation atomizer without valve box cover and without valve element.

FIG. 4 is a view of the valve box cover from the side facing the valve box.

And FIG. 5 is a cross-sectional view of the inhalation atomizer according to the invention.

FIG. 1 shows an inhalation atomizer according to the invention, the housing 1 of which includes an atomizer housing lower part 2 and an atomizer housing upper part 3. The housing can be made of plastic, for example transparent autoclavable plastic such as polypropylene or polysulfone. At the atomizer housing upper part 3 there is arranged a mouthpiece 4 through which the patient inhales the aerosol generated in the inhalation atomizer and into which the patient also exhales. Normally, in an inhalation therapy, the patient is requested not to put down the atomizer after inspiration, i.e. to keep the mouthpiece in the mouth and to exhale into the inhalation atomizer.

In FIG. 1 there is also shown the valve box cover 5 of the inhalation atomizer of the invention. The valve box cover 5 closes the valve box (which is not directly seen in FIG. 1) and has a first cover opening 51 and a second cover opening 52 which communicates the valve box with the surroundings. Through the first cover opening 51 the air which the patient exhales into the mouthpiece 4 during the expiration process flows out of the inhalation atomizer housing. Through the second cover opening 52 ambient air flows into the inhalation atomizer housing during the inspiration process in which the patient inhales through the mouthpiece 4 the aerosol generated in the inhalation atomizer.

In FIG. 2 there is shown the inventive inhalation atomizer without valve box cover 5. Here the valve box 6 and a one-piece valve element 7 can be seen. In FIG. 3 the inventive inhalation atomizer is represented without valve box cover 5 and without valve element 7. Here a partition wall 61 can be seen, which divides the valve box 6 in two sub-chambers 62 and 63.

The first sub-chamber 62 has a first valve box opening 621, which communicates the valve box 6 with the interior of the inhalation atomizer housing. During expiration, the respiration air of the patient flows who exhales into the mouthpiece 4 flows through said opening. For this reason the first valve box opening 621 is arranged relatively near the mouthpiece 4 of the inhalation atomizer. On the side facing the valve box 6 the first valve box opening 621 is formed as a valve seat so that the valve element 7 (see FIG. 2) can close the first valve box opening 621 during the inspiration process. For this purpose the first valve box opening 621 is for instance provided with a peripheral edge 622 shown in FIG. 3, which acts as a sealing lip. The valve element 7, which can be made of a silicone resin, rests on the partition wall 61 so that together with the edge 622 a valve seat is realized. Alternatively, when for instance the first valve box opening 621 is of a circular design, a peripheral edge 622 completely extending along the entire periphery can be provided so that a cooperation with the partition wall 61 is not necessary in order to obtain the desired sealing of the first valve box opening 622 during the inspiration process.

The second sub-chamber 63 has a second valve box opening 631, which communicates the valve box 6 with the interior of the inhalation atomizer housing 1 so that during the inspiration process ambient air can flow into the housing 1 of the inhalation atomizer.

In FIG. 4 the valve box cover 5 is shown in a view in which the side facing the valve box 6 is represented. Here it can be seen that the side of the second cover opening 52 facing the valve box 6 is designed as a valve seat. This is for instance obtained by an edge 521 acting as sealing lip when the valve element 7 abuts against the edge 521 during the expiration process.

As can be seen in FIG. 2, the present inhalation atomizer comprises a valve element 7 which is of a one-piece design. The valve element 7 rests upon the partition wall 61 of the valve box 6. A snap-in projection 611 of the partition wall 61 projects into an opening provided in the valve element 7 whereby the valve element is fixed securely even without the valve box cover 5. Thereby the assembling of the inhalation atomizer after a cleaning by the patient and also during assembly is facilitated.

Figure 1:
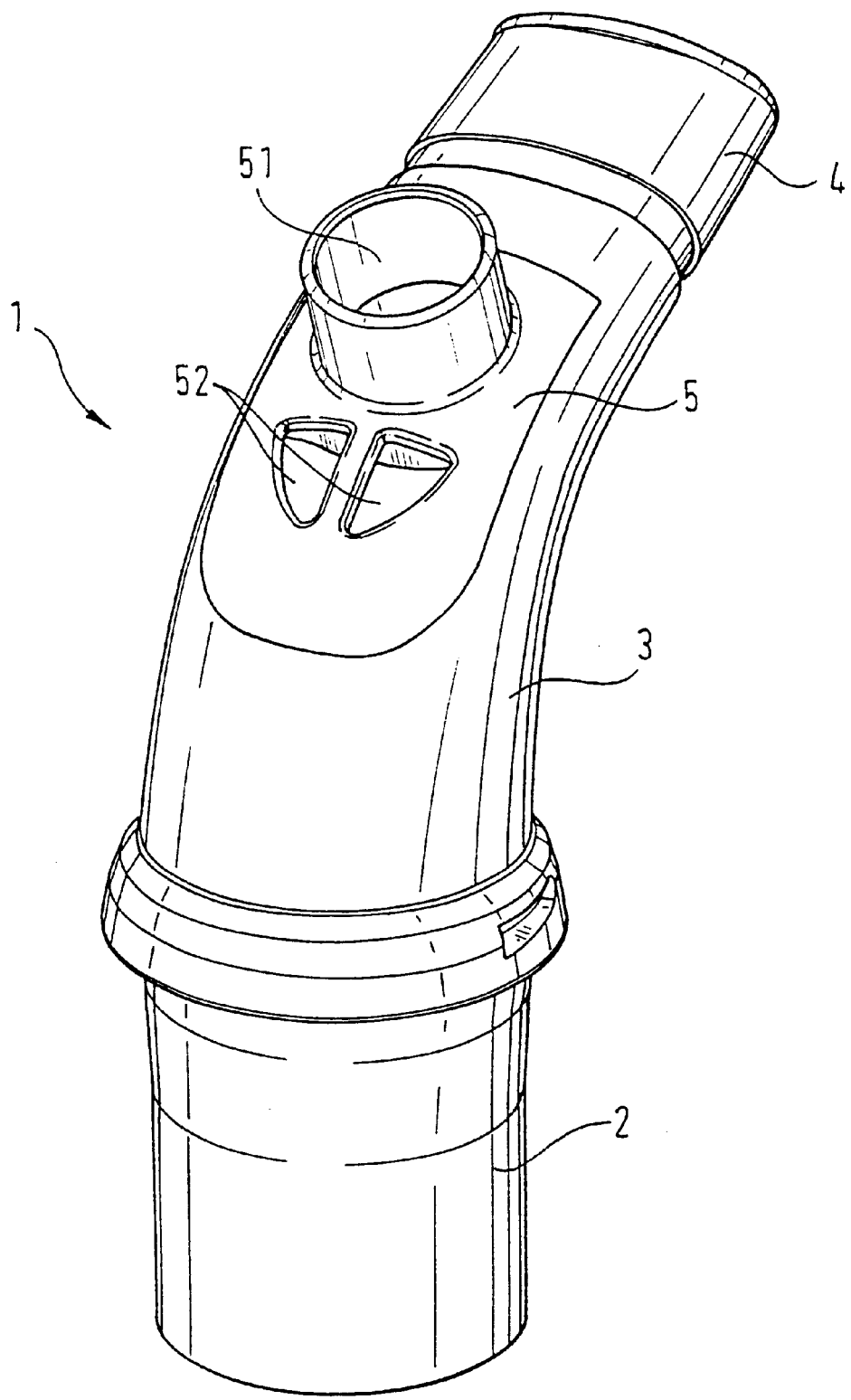
Figure 2:
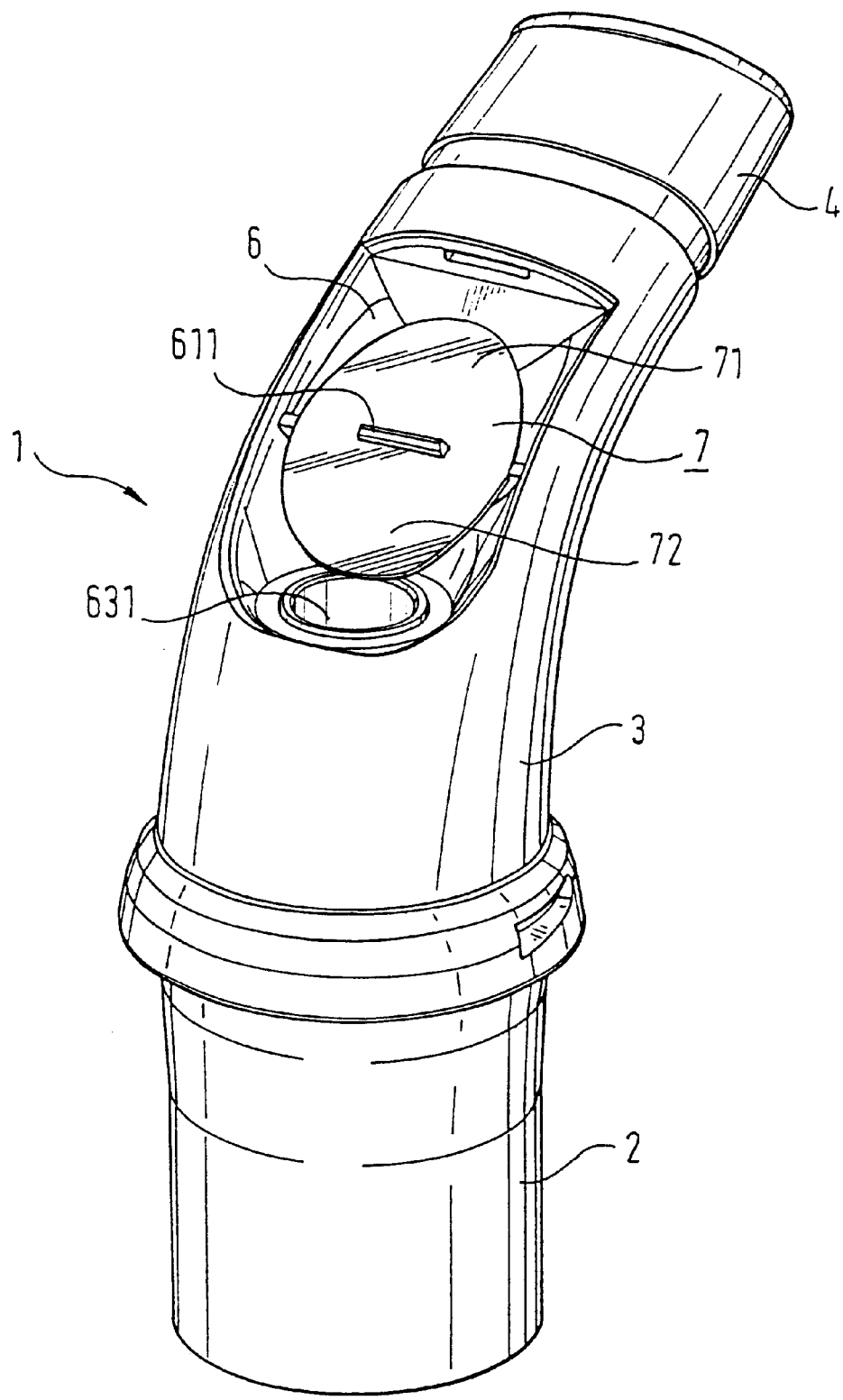
Figure 3:
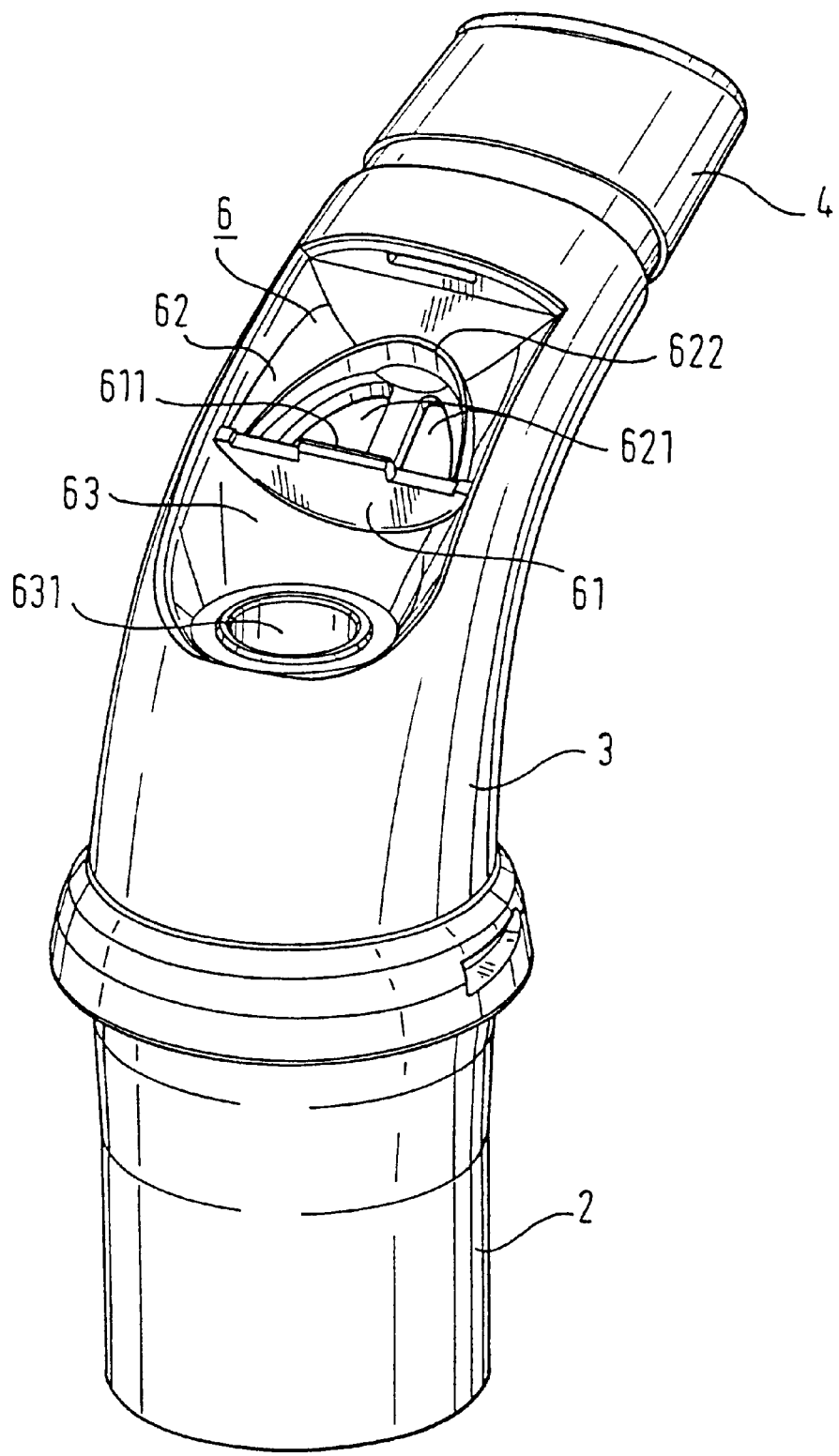
Figure 4:
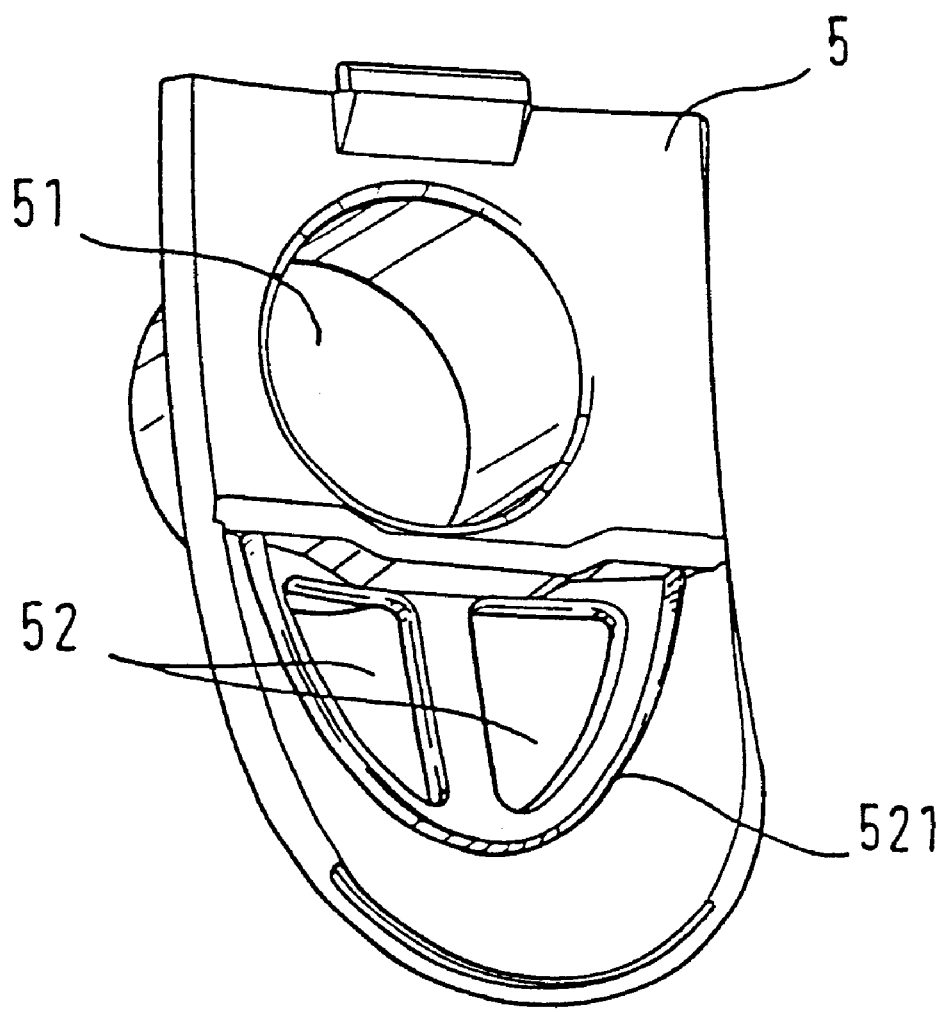
Figure 5:
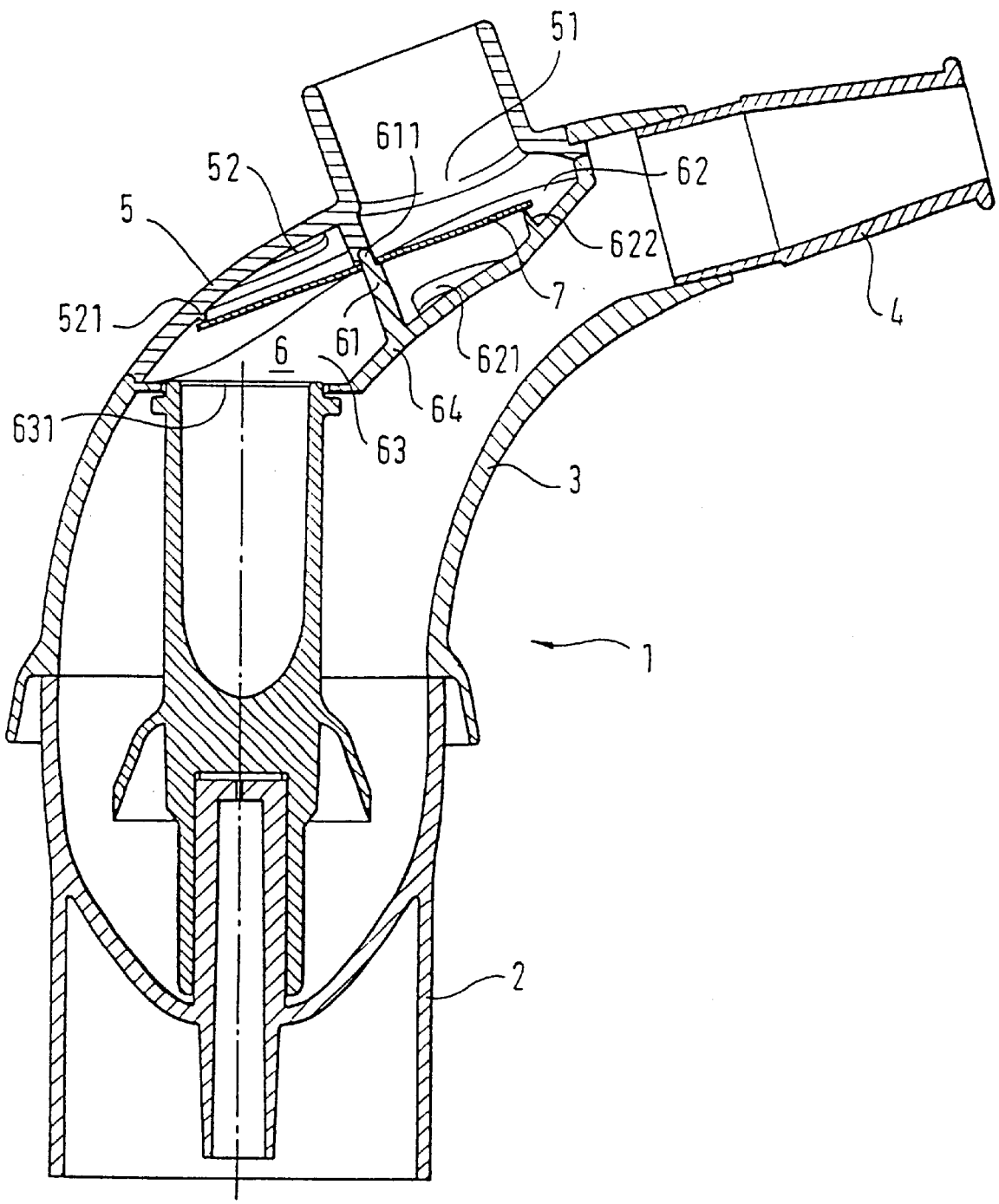

The valve element 7 is, as is shown in FIG. 2, of a symmetrical structure. Thereby a further simplification of the handling is obtained as the patient need not pay any attention to the orientation thereof when inserting the valve element 7. As can be clearly seen from FIGS. 3 and 4 in connection with FIG. 2, the symmetrical design of the valve element 7 is reflected in the symmetrical design of the first valve box opening 621 and the second cover opening 52.

As is shown in FIG. 2, a first section 71 of the valve element 7 lies in the first sub-chamber 62 of the valve box 6. Therein the first section 71 is arranged such that the first section 71 of the valve element 7 rests on the valve seat 622 of the first valve box opening 621 during the inspiration process and closes the same. Thereby it is guaranteed that during the inspiration process the patient inhales the aerosol which is generated in the inhalation atomizer. During the expiration process the first section 71 of the valve element 7 is lifted off the valve seat 622 and opens or releases the first valve box opening 621 without closing the first cover opening 51. The air exhaled by the patient therefore can flow through the mouthpiece 4, the first valve box opening 621, the first sub-chamber 62 and the first cover opening 51.

A second section 72 of the valve element 7 lies in the second sub-chamber 63 of the valve box 6. The second section 72 of the valve element 7 is arranged such that the second section 72 abuts against the valve seat of the second cover opening 52 of the valve box cover 5 during the expiration process. Thereby, during the expiration process, the second section 72 of the valve element 7 closes the second cover opening 52 so that the air exhaled by the patient into the mouthpiece does not cause the aerosol generated in the inhalation atomizer housing 1 to get to the outside together with the exhaled air through the second valve box opening 631, the second subchamber 63 and the second cover opening 52. During the inspiration process the second section 72 of the valve element 7 opens the second cover opening 52 without closing the second valve box opening 631. Thus, during inspiration through the mouthpiece 4, the patient can inhale ambient air through the second cover opening 52, the second sub-chamber 63 and the second valve box opening 631. Therein, the air thus inhaled takes along the aerosol generated in the inhalation atomizer housing 1 and supplies it to the patient via the mouthpiece 4.

FIG. 5 shows the present inhalation atomizer in a general view in cross-section, which is described in the following for a further illustration of the structure of an atomizer according to the invention.

Also in FIG. 5 it is recognized that the housing 1 of the inhalation atomizer comprises a lower housing part 2 and an upper housing part 3. At the upper housing part there is arranged the mouthpiece 4. Furthermore, in the representation of FIG. 5 the valve box 6 can be seen, which is closed towards the outside by the valve box cover 5. The valve box 6 comprises the first sub-chamber 62 and the second sub-chamber 63 which are separated from the housing interior by a wall 64. The valve box 6 communicates with the housing interior via the valve box openings 621 and 631 and towards the surroundings via the openings 51 and 52 of the valve box cover 5. The openings are closed by the flexible valve element 7, which rests upon the partition wall 61 and is secured via a snap-in projection 611 as well as by the clamping effect exerted by the valve box cover 5. Finally, in FIG. 5 the design of the valve seats 622 and 521 can be seen.

What is claimed is:

1. An inhalation atomizer, comprising a housing;

a valve box formed in the housing and divided by a partition wall into first and second sub-chambers, the first sub-chamber having a first valve box opening that communicates the valve box with an interior of the housing and which defines a first valve seat on an outer side of the valve box, the second sub-chamber having a second valve box opening that communicates the valve box with the interior of the housing;

a valve box cover that closes the valve box and has a first cover opening that communicates the first sub-chamber with the outside, and has a second cover opening that communicates the second sub-chamber with the outside and defines a second valve seat on a side of the cover facing the valve box; and a one-piece valve element, comprising a first section disposed in the first sub-chamber such that during an inspiration process the first section rests upon the first valve seat of the first valve box opening, and during an expiration process opens the first valve box opening to permit outflow from the housing, and a second section arranged in the second sub-chamber such that during an expiration process the second section rests upon the second valve seat of the second cover opening and during an inspiration process opens the second cover opening to permit inflow to the housing.

2. The inhalation atomizer of claim 1, wherein the first valve seat of the first valve box opening is defined as an edge extending at the periphery of the first valve box opening.

3. The inhalation atomizer of claim 1, wherein the second valve seat of the second cover opening is defined as an edge extending at the periphery of the second cover opening.

4. The inhalation atomizer according to claim 1, wherein the valve element is of a symmetrical shape.

5. The inhalation atomizer of claim 4, wherein the valve element has equally sized sections that project into the first and second sub-chambers.

6. The inhalation atomizer according to claim 1, wherein the valve element has a snap-in opening.

7. The inhalation atomizer according to claim 6, wherein the partition wall comprises a projection that engages the snap-in opening of the valve element.

8. The inhalation atomizer according to claim 7, wherein the valve element is secured between the partition wall of the valve box and the valve box cover.

9. The inhalation atomizer according to claim 1, wherein the valve element is substantially planar.

* * * * *